United States Patent
Dhanotiya et al.

(10) Patent No.: US 12,114,839 B2
(45) Date of Patent: Oct. 15, 2024

(54) MEDICAL DEVICE HAVING INDEPENDENT ARTICULATION AND METHODS OF USE

(71) Applicant: Boston Scientific Limited, Galway (IE)

(72) Inventors: Aditya Dhanotiya, Indore (IN); Nabarun Bhowmick, Kolkata (IN); Deepak Kumar Sharma, Muzaffarnagar (IN); Subodh Morey, Ponda (IN); Shrikant Vasant Raut, Mumbai (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 181 days.

(21) Appl. No.: 17/477,994

(22) Filed: Sep. 17, 2021

(65) Prior Publication Data
US 2022/0087503 A1 Mar. 24, 2022

Related U.S. Application Data (60) Provisional application No. 63/081,509, filed on Sep. 22, 2020.

(51) Int. Cl.
*A61B 1/008* (2006.01)
*A61B 1/005* (2006.01)
*A61B 1/015* (2006.01)

(52) U.S. Cl.
CPC ............ *A61B 1/008* (2013.01); *A61B 1/0052* (2013.01); *A61B 1/015* (2013.01)

(58) Field of Classification Search
CPC ....... A61B 1/008; A61B 1/0052; A61B 1/015; A61B 1/00042; A61B 1/00094; A61B 1/00098; A61B 1/0125; A61B 1/00073
See application file for complete search history.

(56) References Cited

U.S. PATENT DOCUMENTS

| | | | |
|---|---|---|---|
| 6,743,220 B2 | 6/2004 | Sheffer et al. | |
| 6,971,989 B2 | 12/2005 | Yossepowitch | |
| 7,635,374 B2 | 12/2009 | Monassevitch et al. | |
| 7,637,905 B2 * | 12/2009 | Saadat | A61B 1/0055 606/1 |
| 10,182,712 B2 * | 1/2019 | Matthes | A61B 1/0125 |
| 2013/0041214 A1 * | 2/2013 | Maahs | A61B 1/0051 600/104 |
| 2013/0289351 A1 * | 10/2013 | Ravo | A61B 1/00128 600/113 |
| 2019/0246877 A1 * | 8/2019 | Mitsuya | A61B 1/00066 |
| 2021/0063723 A1 * | 3/2021 | Uchida | A61B 1/005 |
| 2021/0177523 A1 * | 6/2021 | Ebrahimi | A61B 17/24 |

FOREIGN PATENT DOCUMENTS

| | | |
|---|---|---|
| JP | 2010263959 A | 11/2010 |
| WO | 2018170143 A1 | 9/2018 |

* cited by examiner

*Primary Examiner* — John P Leubecker
*Assistant Examiner* — Li-Ting Song
(74) *Attorney, Agent, or Firm* — Bookoff McAndrews, PLLC (57) ABSTRACT

A medical device includes a handle, a shaft extending from the handle, and an articulation member integral with or attached to a distal end of the shaft. The articulation member includes a first portion coupled to a second portion, the second portion is receivable in a slot defined by the first portion, and the handle is coupled to each of the first portion and the second portion and to articulate the first portion independently of articulating the second portion.

16 Claims, 11 Drawing Sheets

MEDICAL DEVICE HAVING INDEPENDENT ARTICULATION AND METHODS OF USE

CROSS-REFERENCE TO RELATED APPLICATIONS

This patent application claims the benefit of priority under 35 U.S.C. § 119 to U.S. Provisional Patent Application No. 63/081,509, filed Sep. 22, 2020, which is herein incorporated by reference in its entirety.

TECHNICAL FIELD

The disclosure relates generally to endoscopic medical devices and related methods of use. For example, the disclosure relates to endoscopic medical tools and methods related to accessing target sites and performing medical procedures at the target sites.

BACKGROUND

In certain medical procedures, it may be necessary to articulate a distal end of an endoscope and/or move portions of the endoscope. For example, an endoscopic medical procedure may require sampling of tissue of the gastrointestinal tract, for example in the esophagus, stomach, or intestines. In these situations, it may be necessary to independently articulate different portions of the distal end of the endoscope.

During an endoscopic procedure, a user generally inserts an endoscope into a body lumen of a patient. The user utilizes a handle of the endoscope to control the endoscope during the procedure. Tools may be passed through a working channel of the endoscope via, for example, a port in the handle, to deliver treatment at the procedure site near a distal end of the endoscope. The procedure site is remote from the operator.

To perform medical procedures, such as to obtain samples of tissue from the gastrointestinal tract, one or more tools may be used to grasp the tissue and remove a portion of the tissue. This procedure may require multiple tools and accessories, which may be difficult for a single user to control and/or require multiple personnel to control various actuation mechanisms associated with each tool. Such systems, however, may result in inconsistent use of the endoscope and associated tool(s), or may not result in the medical procedure being performed properly.

SUMMARY OF THE DISCLOSURE

According to an aspect, a medical device includes a handle, a shaft extending from the handle, and an articulation member integral with or attached to a distal end of the shaft. The articulation member includes a first portion coupled to a second portion, the second portion being receivable in a slot defined by the first portion, and the handle is coupled to each of the first portion and the second portion and configured to articulate the first portion independently of articulating the second portion.

A distalmost end of the second portion may be configured to move distally and proximally relative to a distalmost end of the first portion.

The first portion may be configured to move along a first plane and a second plane, each of the first plane and the second plane perpendicular to a longitudinal axis of the shaft.

The second portion may be configured to move along a first plane perpendicular to a longitudinal axis of the shaft.

The second portion may include a port configured to apply suction for grasping a material.

The handle may include a plurality of actuators, each actuator may be configured to control articulation of the first portion or the second portion.

The device may be a locking mechanism corresponding to each actuator and may be configured to prevent rotational movement of the corresponding actuator.

The handle may include a first actuator rotatable about a first axis of rotation and a second actuator rotatable about a second axis of rotation different from the first axis of rotation.

The second actuator may be distal to the first actuator.

The first actuator may be configured to control articulation of the first portion, and the second actuator may be configured to control articulation of the second portion independent of movement of the first portion.

The device may include a third actuator, where the first actuator may be configured to control articulation of the first portion along a first plane, and the third actuator may be configured to control articulation of the second portion along a second plane, different from the first plane.

The second actuator may be configured to control articulation of the second portion along the first plane.

The third actuator may be rotatable about the first axis of rotation.

The device may further include a fourth actuator coupled to the handle and rotatable about the first axis of rotation, where the fourth actuator may be configured to move the second portion in a proximal direction, a distal direction, or both a proximal direction and a distal direction.

The handle may include a port in communication with a lumen extending through the shaft and the articulation member, the lumen terminating at a distal opening in the first portion of the articulation member.

According to another aspect, a medical device includes a handle, a shaft coupled to the handle, and an articulation member integral with or coupled to a distal end of the shaft, the articulation member forming a distalmost end of the medical device and having a first portion coupled to a second portion. The first portion is configured to move along a first plane and along a second plane independently of the first plane, and the second portion is configured to move along the first plane independent of movement of the first portion along each of the first plane and the second plane.

The handle may include a first actuator and a second actuator each rotatable about a first axis of rotation to control articulation of the first portion, and the handle may include a third actuator rotatable about a second axis of rotation different from the first axis of rotation to control articulation of the second portion.

The handle may include a fourth actuator configured to control proximal and distal movement of the second portion relative to the first portion.

The fourth actuator device may be rotatable about the first axis of rotation.

According to another aspect, a method for treating a patient includes inserting a distal end of a shaft into an opening in a patient, wherein the distal end includes an articulation member having a first portion coupled to a second portion, advancing the distal end to a target site, actuating a first actuator to move the second portion relative to the first portion, grasping tissue at the target site via the second portion, and performing a medical procedure using a medical tool extending from a distal opening of the first portion.

BRIEF DESCRIPTION OF THE DRAWINGS

The accompanying drawings, which are incorporated in and constitute a part of this application, illustrate various exemplary embodiments and together with the description, serve to explain the principles of the present disclosure and exemplary embodiments.

DETAILED DESCRIPTION

The disclosure is described with reference to exemplary medical systems for performing medical procedures using a scope (e.g., endoscope, uteroscope, bronchoscope, duodenoscope, colonoscope, or the like) on a target site. The devices associated with the medical systems may improve the functionality of the scope by allowing a single operator or user to independently control different portions of a distal end of the scope, and/or to independently control one or more tools passed through the scope to the target site. In examples, multiple actuators provided on a handle of the scope may provide independent actuation of different portions of the distal end of the scope controllable by a single user.

Reference to any particular procedure is provided in this disclosure only for convenience and not intended to limit the disclosure. A person of ordinary skill in the art would recognize that the concepts underlying the disclosed devices and methods may be utilized in any suitable procedure. The disclosure may be understood with reference to the following description and the appended drawings, wherein like elements are referred to with the same reference numerals.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus.

For ease of description, portions of the device and/or its components are referred to as proximal and distal portions. It should be noted that the term "proximal" is intended to refer to portions closer to a user of the device, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/-10% of a stated or implied value. Additionally, terms that indicate the geometric shape of a component/surface include approximate shapes.

Figure 1:
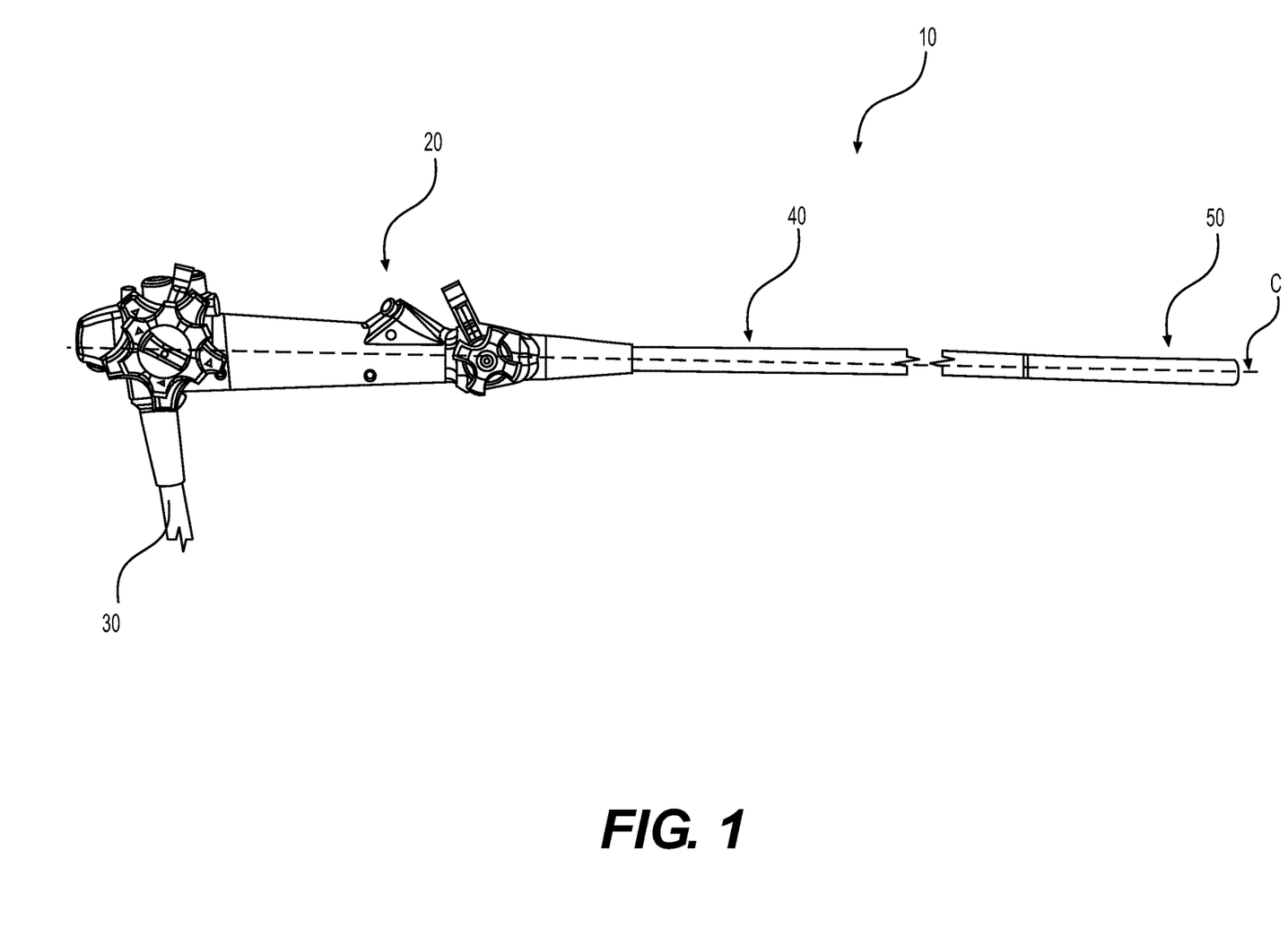
FIG. 1 is a schematic of a medical system according to one or more aspects of the present disclosure.

Referring to FIG. 1, a medical system 10 (also referred to herein as a medical device) according to some examples of the present disclosure is shown. Medical system 10 includes a flexible shaft 40 (e.g., a catheter), a handle 20 coupled to a proximal end of flexible shaft 40, and an articulation member 50. The articulation member 50 may be a separate component attached to a distal end of shaft 40, or the articulation member 50 may be a distal portion of the shaft 40 (e.g., at least a portion of the articulation member 50 being integral with the shaft 40). Medical system 10 may include one or more lumens each extending through shaft 40 and articulation member 50. Handle 20 includes multiple actuating devices (e.g., actuators) which control articulation of articulation member 50 in multiple directions, and movement of associated components and tools, as will be described herein. Handle 20, shaft 40, and articulation member 50 extend along a longitudinal axis C, which may define a neutral position of articulation member 50.

Figure 2A:
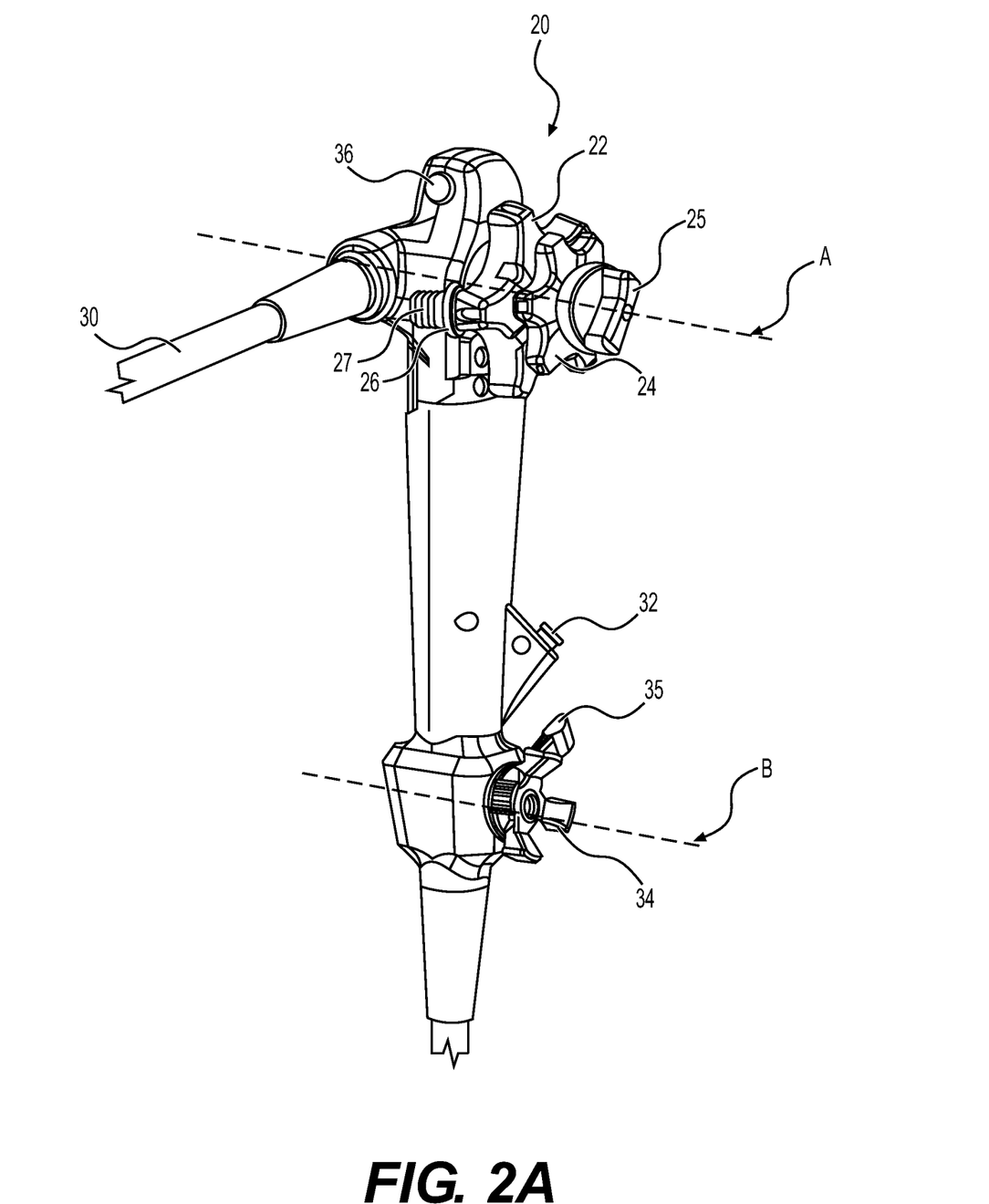
FIGS. 2A and 2B are side views of a handle of the delivery system of FIG. 1.

With reference to FIG. 2A, handle 20 may include one or more ports 32 for inserting and/or removing tools, fluids, or other materials into and/or from the patient via shaft 40. Port 32 may be used to introduce one or more medical tools through a lumen (e.g., a working channel) of shaft 40 and articulation member 50 (e.g., FIG. 3B showing a distal end of medical tool 44 extending from a distal opening 42 of a lumen of shaft 40 and articulation member 50). Medical tool 44 may be any tool, such as, but not limited to, a snare, a knife, forces, an ablation laser, or other suitable tool for performing a medical procedure. Distal opening 42 may be disposed in a distal end face of a first portion 52 of articulation member 50 and may face distally. The lumen may also be in communication with an umbilicus 30 (FIGS. 1 and 2A) for introducing fluid and/or providing suction to the lumen, which may be introduced from umbilicus 30 to a target site via distal opening 42. In addition, one or more electrical cables (not shown) may extend from the proximal end of medical system 10 and/or umbilicus 30 to articulation member 50 and may provide a user with electrical control over imaging, lighting, and/or other electrical devices or components of medical system 10. Such electrical cables may carry imaging signals from the distal end of flexible shaft 40 proximally to be processed and/or displayed on a display.

Figure 3A:
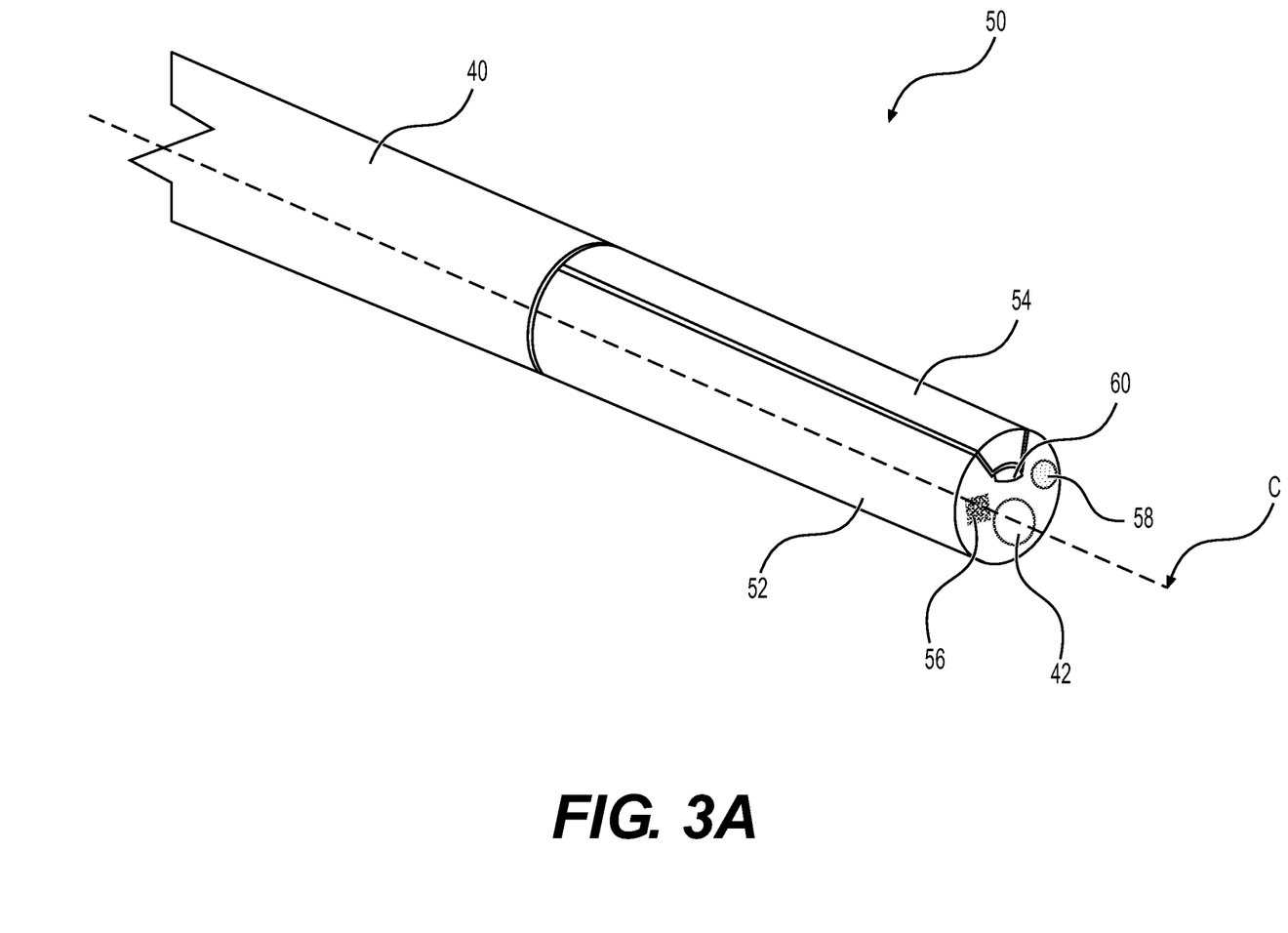
FIGS. 3A and 3B are side views of a distal end of the medical system of FIG. 1.
Figure 3B:
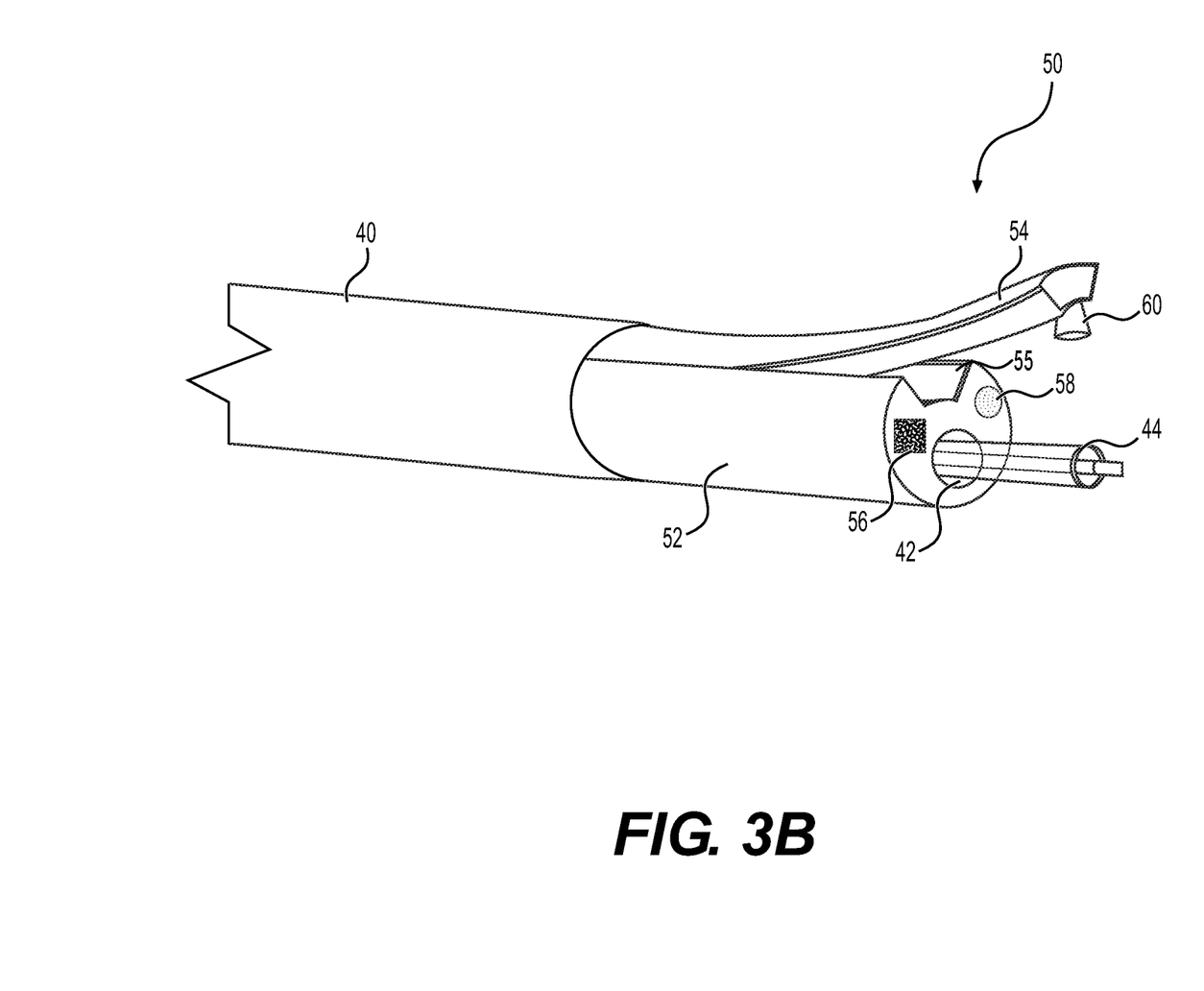

Articulation member 50 is shown in FIGS. 3A and 3B. Articulation member 50 includes a first portion 52 and a second portion 54. First portion 52 may be integral with shaft 40, for example, or may be a separate component coupled to shaft 40. First portion 52 may include a slot 55 as shown in FIG. 3B. Second portion 54 may be received in slot 55 in a neutral position (e.g., a first position). Slot 55 may have a size and shape approximately equal to the size and shape of second portion 54. During an insertion of medical system 10, second portion 54 may be in the neutral position. As will be described herein, second portion 54 may move relative to first portion 52. Such movement may expose a port 60 on or proximate a distal end of second portion 54. Port 60 may be a vacuum port and may assist in grasping tissue or other material during a medical procedure. Alternatively, port 60 may include a hook or other device configured to grasp tissue. As will be described herein, each of first portion 52 and second portion 54 may be articulated independently or together.

With reference to FIG. 3A, first portion 52 may include one or more lumens each having a distal opening 42, one or more imagers 56 (e.g., a camera or other imaging device), and one or more illumination devices 58 (e.g., a light emitting device). A plurality of lumens may extend through shaft 40 to connect the proximal end of shaft 40 (and/or handle 20 or umbilicus 30) to respective opening 42, imager 56, and/or illumination device 58. The one or more electrical cables (not shown) may extend from the proximal end of medical system 10 and/or umbilicus 30 to imager 56 and/or illumination device 58, and may provide electrical controls for imaging and/or lighting, and may carry imaging signals proximally to be processed and/or displayed on a display. The electrical cables may pass through corresponding lumens in shaft 40.

Figure 2B:
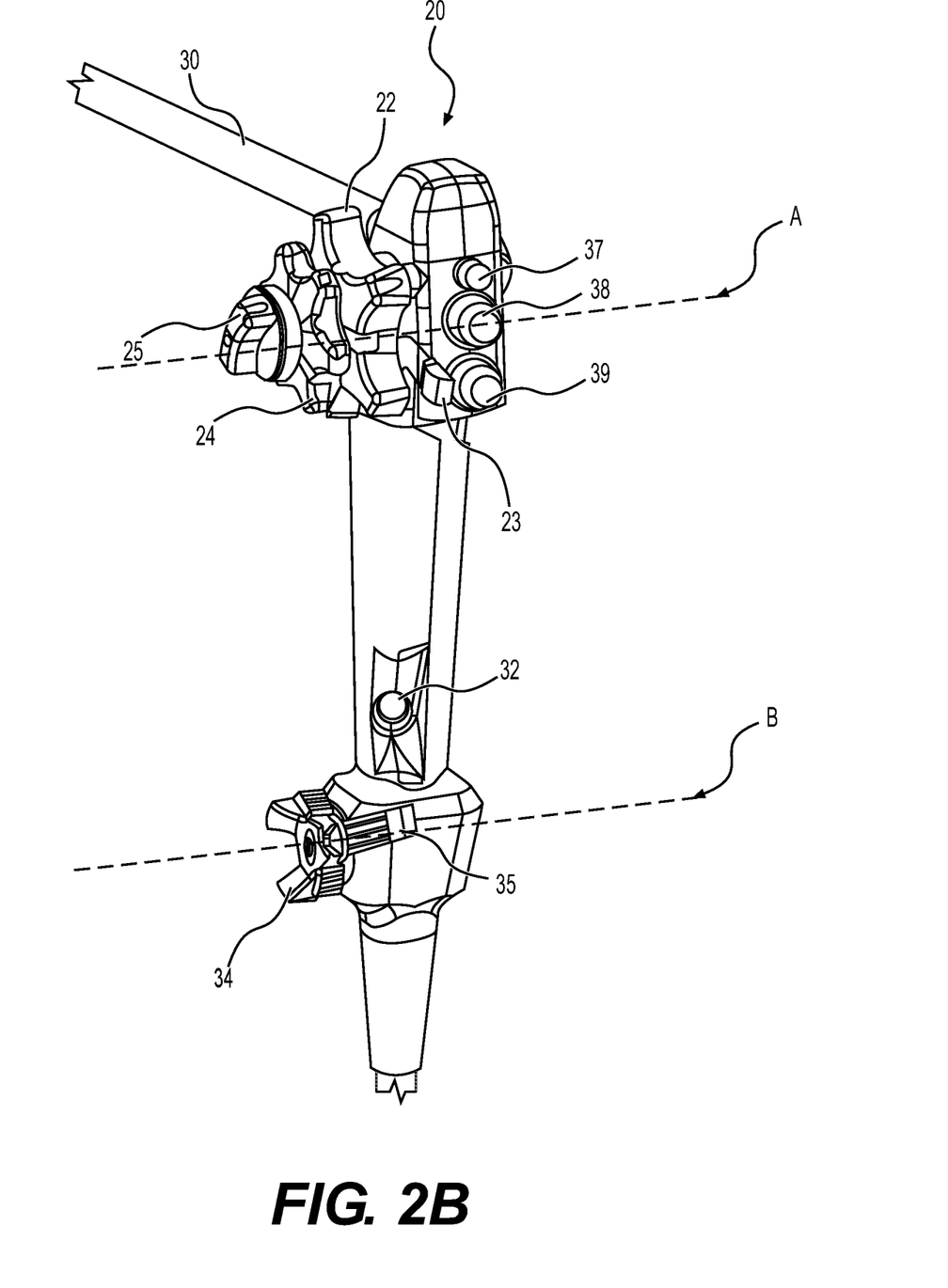

FIGS. 2A and 2B illustrate actuators 36, 37, 38, 39, which may control imaging, suction, or the like. For example, actuation of imager 56 may be controlled by engaging actuator 36 (FIG. 2A). In some instances, depressing or otherwise engaging actuator 36 a first time may activate imager 56, while depressing or otherwise engaging actuator 36 a second time may deactivate imager 56. Similarly, depressing or otherwise engaging actuator 37 a first time may activate a vacuum source in communication with medical system 10 to generate suction or vacuum at port 60 of second portion 54. The suction may allow a user to grasp tissue or other material in a patient's body via port 60 and manipulate the tissue by articulating second portion 54, as will be described herein. Depressing or otherwise engaging actuator 37 a second time may deactivate the vacuum source, thereby releasing the tissue or material from port 60. Actuators 38 and 39 may operate in a similar manner. For example, depressing or otherwise engaging respective actuators 38, 39 a first time may activate suction or release air (or other gas suitable for use in a body cavity), respectively, via distal opening 42. This may allow the user to remove debris from distal opening 42 and/or from the lumen connected to distal opening 42 by (1) suctioning the debris through the lumen to the attached umbilicus 30, or (2) expelling the debris into the body via distal opening 42. Depressing or otherwise engaging actuators 38, 39 a second time may deactivate the suction or air/gas sources. It will be understood that actuators 36-39 may be any actuator known for use with medical devices (e.g., button, switch, lever, etc.) for actuating suction and/or imaging devices. Further, a user may depress or otherwise engage each actuator 36-39 more than once and/or in a specific sequence to activate and/or deactivate the corresponding elements. The handle 20 may include an actuator similar to any of actuators 36-39 to control illumination device 58. Alternatively, or additionally, imaging, suction, lighting, and other operations may be controlled via a user interface, such as a graphical user interface (GUI) (not shown) or the like.

With continued reference to FIGS. 2A and 2B, handle 20 may include additional actuators, e.g., devices 22, 24, 26, 34 as shown, for controlling different degrees of freedom of articulation member 50. Devices 22, 24, 26, 34 may be, for example, actuators in the form of rotatable knobs or levers that rotate about their axes to push/pull actuating elements (not shown) and/or move portions of articulation member 50 in proximal and/or distal directions. The actuating elements, such as cables or wires suitable for medical procedures (e.g., medical grade plastic or metal), may extend distally from a proximal end of medical system 10 and connect to corresponding elements of articulation member 50 to control movement thereof.

Articulation control devices 22, 24 (e.g., articulation control knobs) are connected to a proximal end of handle 20. Devices 22, 24 may be connected to handle 20 via a pin or other similar component that defines a rotational axis A. Devices 22, 24 are configured to rotate clockwise and counterclockwise about rotation axis A. Devices 22, 24 are each coupled to first portion 52 of articulation member 50 via one or more control elements (e.g., articulation wires) and may cause first portion 52 to move in a left-right direction and/or in an up-down direction.

Device 22 may be attached to handle 20 along axis A closer to handle 20 in a radial direction than device 24. Device 22 may control an up/down movement of first portion 52 (e.g., movement along a first plane), while device 24 may control a right/left movement of first portion 52 (e.g., movement along a second plane perpendicular to the first plane). It will be understood that device 22 may control the left/right movement of first portion 52, and device 24 may control the up/down movement of first portion 52.

Figure 4A:
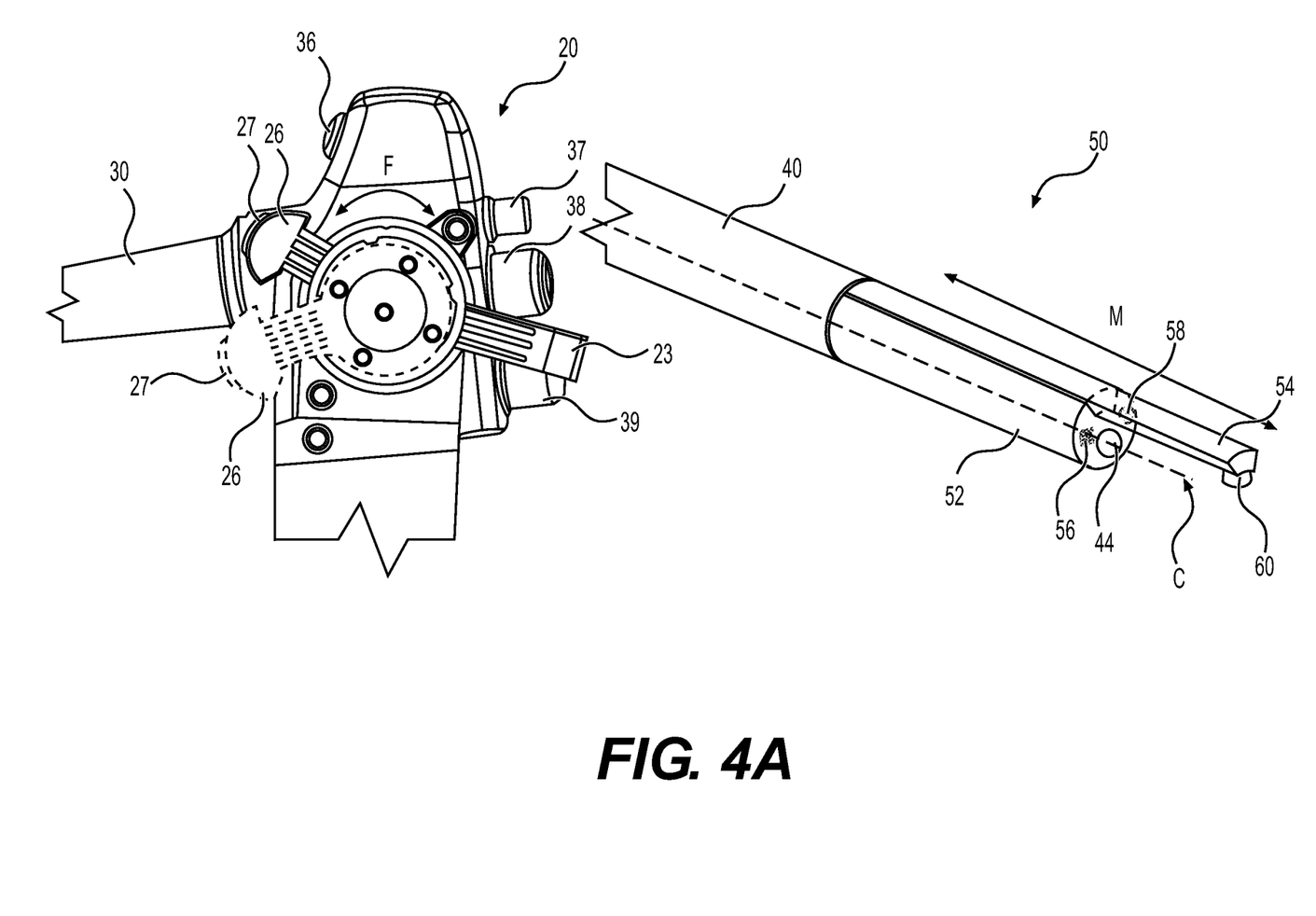
FIGS. 4A-4D are side views of portions of the handle and the distal end of the medical system of FIG. 1.
Figure 4B:
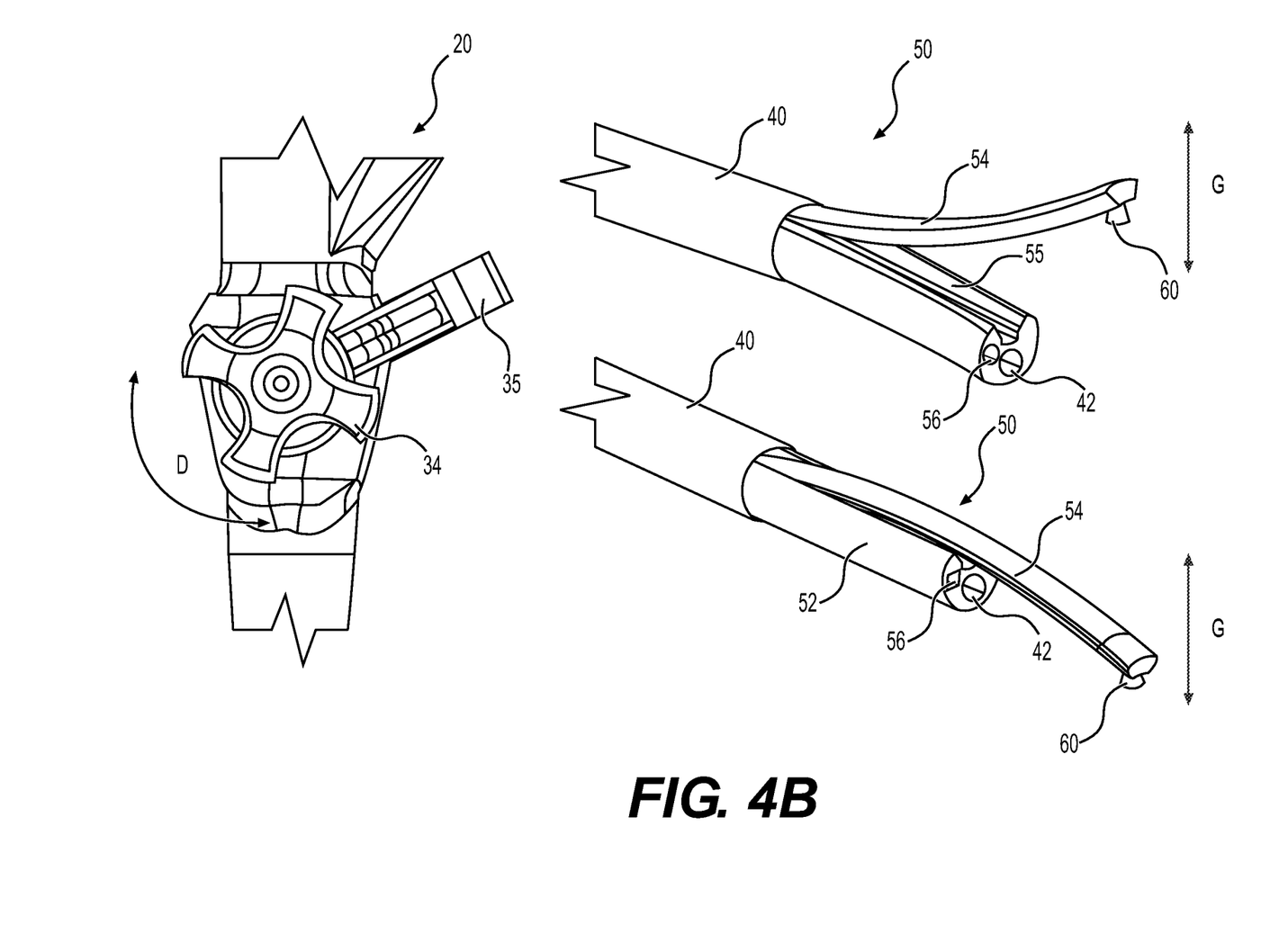
Figure 4C:
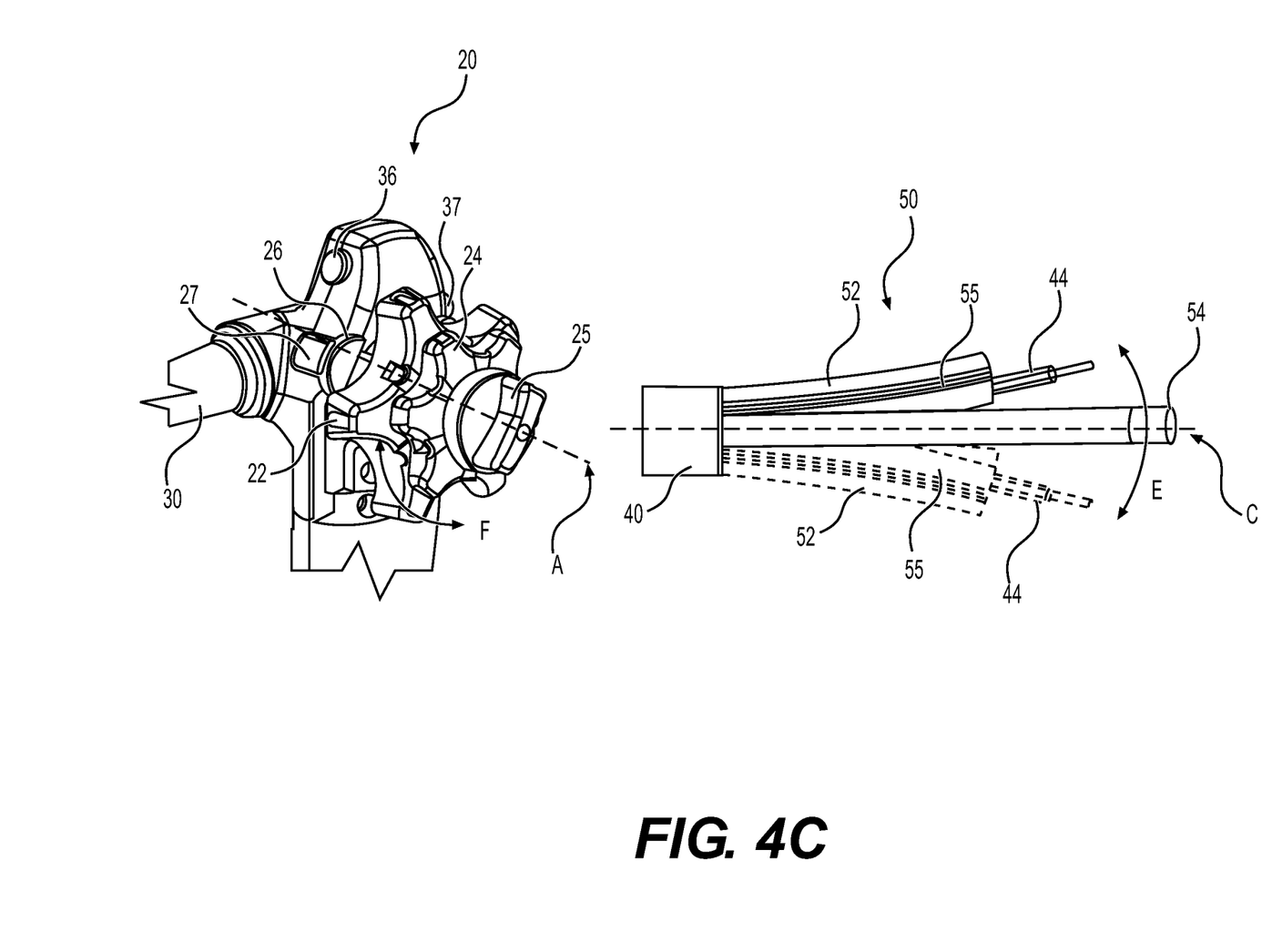
Figure 4D:
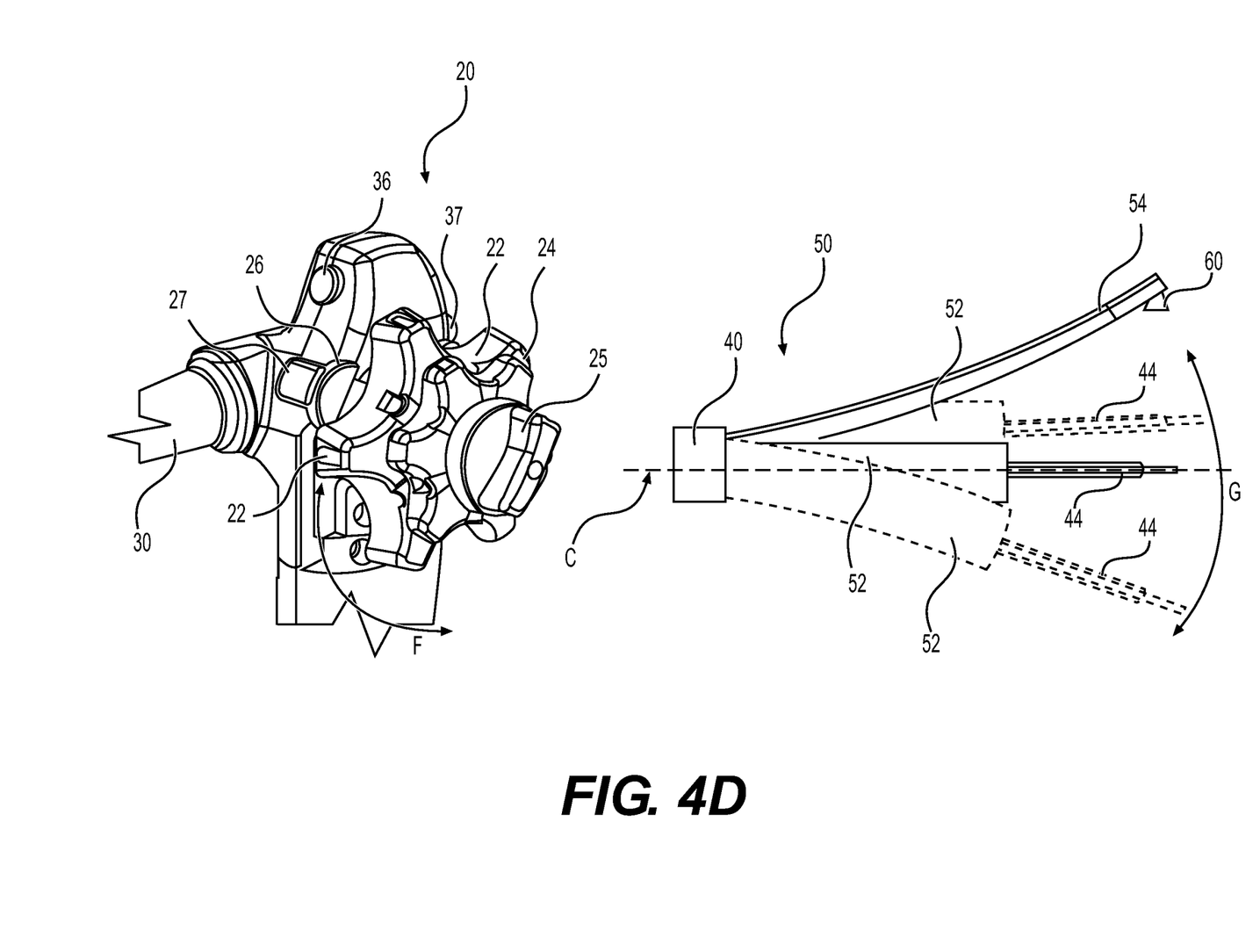

As an example, articulation of first portion 52 of articulation member 50 is shown in FIG. 4D. FIG. 4D illustrates second portion 54 extending away from first portion 52 (extending above first portion 52 in FIG. 4D), as will be described herein. A user may rotate device 22 about axis A in clockwise and counterclockwise directions, indicated by arrow F. Rotation of device 22 about axis A in a clockwise direction, for example, may cause articulation wires to be pulled or pushed, and may cause first portion 52 to move from a neutral position (where first portion 52 lies along a longitudinal axis C) in a direction up from the neutral axis, indicated by arrow G (shown in dotted lines above longitudinal axis C in FIG. 4D). Rotation of device 22 about axis A in the opposite direction (e.g., counterclockwise) may cause articulation wires to be pulled or pushed, and may cause first portion 52 to move back downwards in FIG. 4D, toward the neutral position (shown by the solid lines in FIG. 4D). Continued rotation of device 22 may cause first portion 52 to move downwards relative to the neutral position shown in FIG. 4D, as shown by the dotted lines below longitudinal axis C. Since medical tool 44 may extend distally of distal opening 42 in first portion 52, articulation of first portion 52 may cause a similar movement of medical tool 44.

A locking mechanism 23 for device 22 is shown in FIG. 2B. Locking mechanism 23 may be a lever or any other device having an axis of rotation, and may be rotated about axis A between a first position and a second position. In the first position, locking mechanism 23 may allow device 22 to rotate about axis A, controlling the up-down movement of first portion 52. In the second position, locking mechanism 23 may prevent device 22 from rotating about axis A. For example, moving locking mechanism 23 to the second position may cause locking mechanism 23 to move in a radially outward direction along axis A and into contact with device 22, thereby increasing frictional force between locking mechanism 23 and device 22 to prevent rotational movement of device 22. Alternatively, or additionally, protrusions or other gear-like members may interlock when locking mechanism 23 contacts device 22, preventing device 22 from rotating about axis A. When a desired position of first portion 52 in the up-down direction is achieved, a user may rotate locking mechanism 23 from the first position to the second position, locking first portion 52 in the desired up-down position. Rotation of locking mechanism 23 back to the first position allows a user to again rotate device 22 about axis A to move first portion 52 in the up-down direction.

Device 24 may also be rotated about axis A in a direction indicated by arrow F in FIG. 4C. FIG. 4C illustrates second portion 54 extending away from first portion 52 (extending out of the page in FIG. 4C), as will be described herein.

Rotation of device 24 about axis A in a clockwise direction, for example, may cause articulation wires to be pulled or pushed, and may cause first portion 52 to move from the neutral position (where first portion 52 lies along longitudinal axis C) in a direction right of the neutral axis, indicated by arrow E (e.g., in the down direction in FIG. 4C and shown in dotted lines). Rotation of device 24 about axis A in an opposite direction (e.g., a counterclockwise direction) may cause articulation wires to be pulled or pushed, and may cause first portion 52 to move to the left (in an upwards direction in FIG. 4C), toward the neutral position. Continued rotation of device 24 may cause first portion 52 to move left of the neutral position (above longitudinal axis C in FIG. 4C), as illustrated by the solid lines of first portion 52 in FIG. 4C.

A locking mechanism 25 for device 24 is shown in FIGS. 2A and 2B. Locking mechanism 25 may be a knob, rotatable device, or any other device having an axis of rotation, and may be rotated about axis A between a first position and a second position. In the first position, locking mechanism 25 may allow device 24 to rotate about axis A, thereby controlling the right-left movement of first portion 52 of articulation member 50. In the second position, locking mechanism 25 may prevent device 24 from rotating about axis A. Rotating locking mechanism 25 to the second position may allow locking mechanism 25 to move in a radial inward direction along axis A and into contact with device 25, thereby increasing frictional force against device 24. Alternatively, or additionally, protrusions or other gear-like members may interlock when locking mechanism 25 may contact device 24, similar to locking mechanism 23 described herein. The increased friction and/or the interlocking of protrusions may prevent device 24 from rotating about axis A. When a desired position of first portion 52 is achieved in the left-right direction, a user may rotate locking mechanism 25 from the first position to the second position, locking first portion 52 in the desired left-right position. Rotation of locking mechanism 25 back to the first position allows a user to again rotate device 24 about axis A to move first portion 52 in the left-right direction. Locking mechanisms 23, 25 allow independent control over devices 22, 24 and corresponding movement of first portion 52. That is, one of devices 22, 24 may be locked while the other of devices 22, 24 may be unlocked, allowing for movement of articulation member 50 in a single plane. Alternatively, devices 22, 24 may be both locked, or may be both unlocked, allowing articulation member 50 to move in multiple planes at the same time, or to prevent movement of articulation member 50.

Figure 2C:
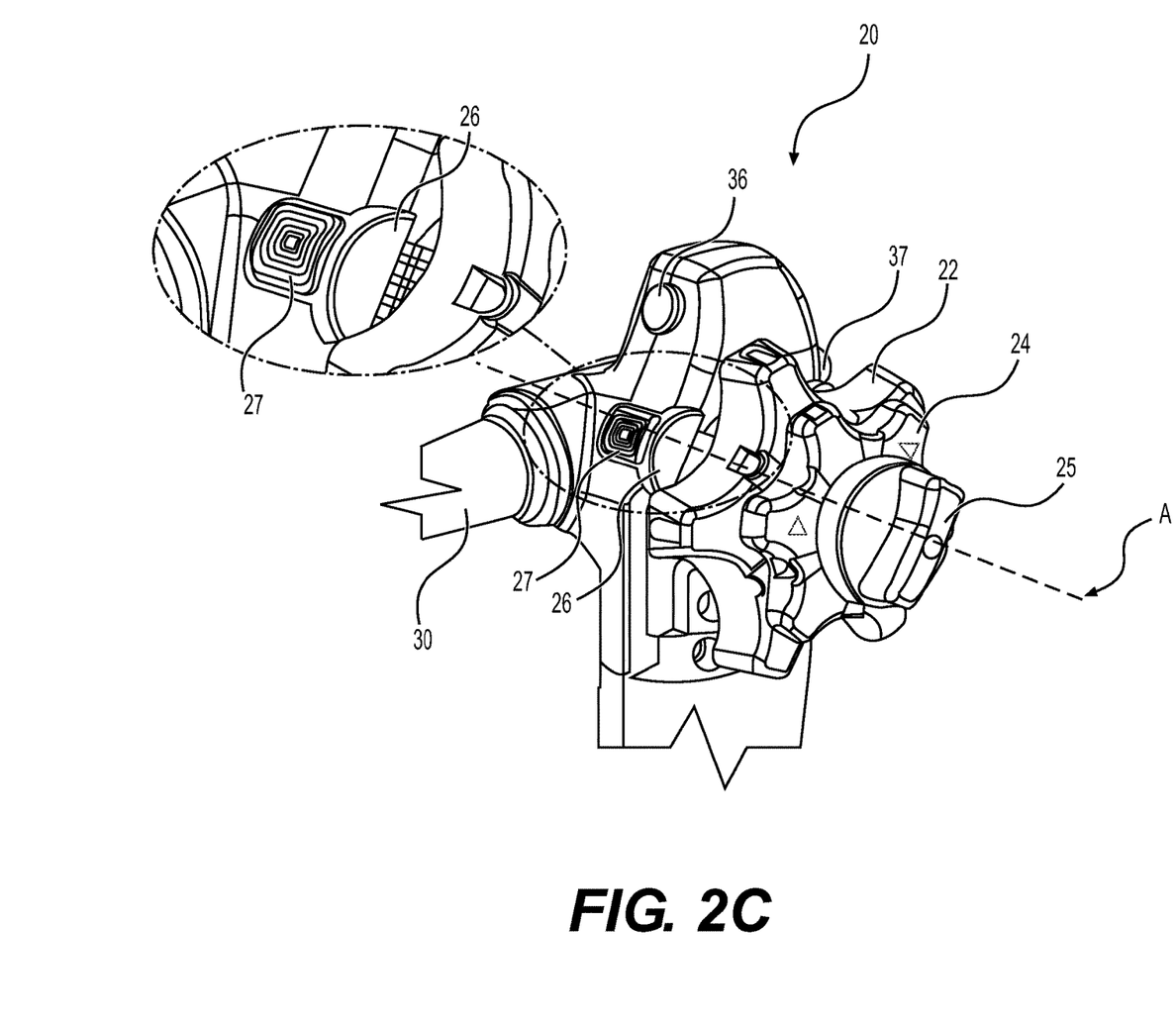
FIG. 2C is a side view of a proximal end of the handle of FIGS. 2A and 2B.

With reference to FIGS. 2A and 2C, the handle 20 may include a device 26, e.g., actuator, for changing a length of articulation member 50 by moving second portion. According to an example, device 26 may include a lever rotatable about axis A of handle 20. Device 26 may be positioned along axis A radially inward of locking mechanism 23, but is not limited to this position along axis A. As shown in FIG. 4A, device 26 may move from a first position (the solid line drawing of device 26) to a second position (the dashed line drawing of device 26); for ease of understanding, devices 22, 24 and locking mechanism 25 are not shown in FIG. 4A. When device 26 is in the first position, a distalmost end of second portion 54 of articulation member 50 may be flush with a distalmost end of first portion 52 (e.g., FIG. 3A). As device 26 is rotated in a counterclockwise direction, indicated by arrow F in FIG. 4A, second portion 54 moves distally (as shown by arrow M) along longitudinal axis C such that the distalmost end of second portion 54 extends distally of the distalmost end of first portion 52. Movement of second portion 54 may be caused by a wire or cable connected to device 26 and second portion 54 at, e.g., a proximal end of second portion 54. As device 26 is rotated to the second position, the wire may push against the proximal end of second portion 54 to move device 26 distally. Rotation of device 26 in an opposite direction (e.g., a clockwise direction) may cause the wire to pull second portion 54 in the proximal direction (indicated by arrow M) until second portion 54 is returned to the first position (where the distalmost ends of first portion 52 and second portion 54 are flush). In some instances, device 26 may continue to be rotated to move second portion 54 proximally of the first position, such that the distalmost end of second portion 54 is proximal of the distalmost end of first portion 52 (e.g., a third position).

Device 26 may also include a locking mechanism 27. As shown in FIGS. 2C and 4A, locking mechanism 27 may be a button or other actuator that may be pushed to lock a rotational position of device 26 relative to axis A. Actuation of locking mechanism 27 may cause an element to extend into a gear-like configuration on handle 20 to prevent rotational movement of device 26 about axis A. A second actuation of locking mechanism 27 may cause the element to be released (e.g., via a spring or the like) from the gear-like configuration to allow rotational movement of device 26 about axis A. In this manner, movement of second portion 54 may be prevented when locking mechanism 27 is in the locked position. It will be understood that locking mechanism 27 may be any locking device used with medical devices or endoscopes to prevent rotational movement of knobs or related devices.

Another device 34, e.g., actuator, for controlling another degree of freedom of second portion 54 of articulation member 50 is shown in FIG. 2A. As described herein, device 34 may be a knob or other suitable actuator or rotatable mechanism and may be configured to rotate about an axis B. Axis B may be approximately parallel to axis A and is located distally of axis A along handle 20. It will be understood, however, that axis B may be proximal to axis A along handle 20 in certain situations, depending on various factors, such as ergonomics or other factors for creating a user-friendly handle 20. Device 34 operates similarly to device 22 in that device 34 may cause second portion 54 to move in the up-down direction relative to longitudinal axis C. As shown in FIG. 4B, rotation of device 34 about axis B as indicated by arrow D may cause second portion 54 to move in the up-down direction, indicated by arrow G. For example, rotation of device 34 in the clockwise direction may cause second portion 54 to move upwards away from first portion 52 in FIG. 4B, while rotating device 34 in the counterclockwise direction may cause second portion 54 to move downwards towards first portion 52 in FIG. 4B (see top and bottom portions of FIG. 4B, the movement of second portion 54 indicated by arrow G).

With continued reference to FIGS. 2A and 4B, a locking mechanism 35 may rotate about axis B and may prevent rotational movement of device 34 and, thereby, prevent articulation of second portion 54 of articulation member 50. Locking mechanism 35 may be a lever, similar to locking mechanism 23, but is not limited thereto. In a first position, locking mechanism 35 may allow device 35 to rotate about axis B, controlling the up-down movement of second portion 52. In the second position, locking mechanism 35 may prevent device 34 from rotating about axis B. Similar to locking mechanism 23, moving locking mechanism 35 to the second position may cause locking mechanism 35 to move in a radially outward direction along axis B and into contact with device 34, thereby increasing frictional force between locking mechanism 35 and device 34 to prevent rotational movement of device 34. Alternatively, or additionally, protrusions or other gear-like members may interlock when locking mechanism 35 contacts device 34, preventing device 34 from rotating about axis B as described herein. When a desired position of second portion 54 in the up-down direction is achieved, a user may rotate locking mechanism 35 from the first position to the second position, locking second portion 54 in the desired up-down position. Rotation of locking mechanism 35 back to the first position allows a user to again rotate device 34 about axis B to move second portion 54 in the up-down direction.

Figure 5:
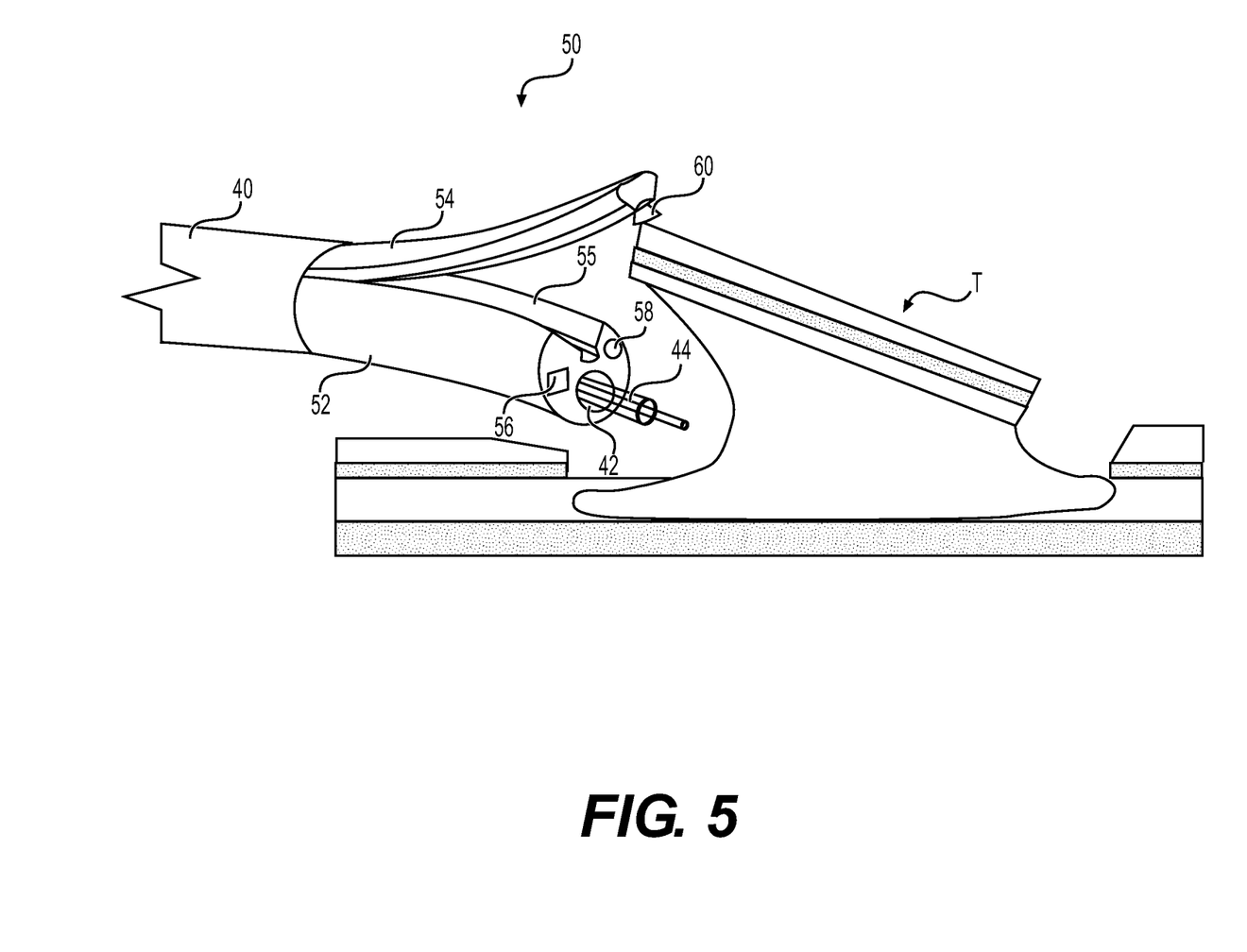
FIG. 5 is a side view of the distal end of the medical system of FIG. 1 at a target site.

A method of performing a medical procedure on a target site using medical system 10 will be described with reference to FIG. 5. Articulation member 50 is inserted into the body via an opening (a natural orifice or an incision in the patient). Alternatively, articulation member 50 may be advanced to the target site via an access catheter (not shown) previously positioned within the body. In some instances, articulation member 50 is advanced with the distalmost ends of first portion 52 and second portion 54 flush. Alternatively, the distalmost ends of first portion 52 and second portion 54 may be offset during insertion.

Once articulation member 50 is positioned at the target site, portions 52, 54 may be independently articulated to perform a medical procedure. For example, device 26 may be actuated to move second portion 54 distally of first portion 52, and device 34 may be actuated to move second portion 54 up or down relative to longitudinal axis C. Once port 60 is positioned adjacent the target site, the user may activate actuator 37 to create a suction or vacuum at port 60. This may allow port 60 to grasp a portion of tissue T at the target site.

Once tissue T is grasped by port 60, the user may articulate first portion 52 using devices 22, 24 to move first portion 52 up-down and/or left-right, respectively, relative to longitudinal axis C. In this manner, the user may control the position of medical tool 44 extending through a lumen of first portion 52. For example, medical tool 44 may be pre-positioned within port 32, and may be advanced distally of distal opening 42 once articulation member 50 is positioned adjacent the target site. Actuating devices 22, 24 may allow the user to control articulation of first portion 52 and, thus, a position of tool 44 relative to the target site. In this manner, the user may cut tissue T and/or perform other medical procedures at the target site. Additionally, the user may activate one or more of actuators 36, 38, 39 to provide imaging, lighting, and/or supply suction or gas via distal opening 42 during the medical procedure.

Once tissue T is removed from the target site, shaft 40 and articulation member 50 may be moved in a proximal direction. In this manner, the user may remove the tissue T from the body for analysis or other additional procedures. Alternatively, suction via port 60 may be deactivated, and tissue T may be released within the body. In this manner, second portion 54 may be realigned with slot 55 in first portion 52, such that the distalmost ends of first and second portions 52, 54 are flush. At this time, articulation member 50 and shaft 40 may be removed from the body. It will be understood that various tools 44 may be inserted and removed from port 32 and advanced to and/or distally of distal opening 42 during the medical procedure. It will be understood that each tool 44 advanced to and/or from distal opening 42 may be moved in the up-down and/or left-right directions via devices 22, 24 acting on first portion 52.

Medical system 10 may allow a single user to operate a scope having a distal end having multiple portions that are capable of articulating and/or moving proximally and/or distally relative to each other. In this manner, the user may be able to perform a medical procedure in a more timely and/or cost effective manner, while minimizing harm to a patient which may be cause by multiple users performing the medical procedure. It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a handle, including;
      a first actuator rotatable about a first axis,
      a second actuator rotatable about a second axis, different from the first axis of rotation;
      a third actuator; and
      a fourth actuator rotatable about the first axis of rotation;
   a shaft extending from the handle; and
   an articulation member integral with or attached to a distal end of the shaft, wherein the articulation member includes a first portion coupled to a second portion, the second portion being receivable in a slot defined by the first portion;
   wherein the handle is coupled to each of the first portion and the second portion,
   wherein the first actuator is configured to control articulation of the first portion along a first plane,
   wherein the third actuator is configured to control actuation of the first portion along a second plane, different from the first plane, and
   wherein the fourth actuator is configured to move the second portion in a proximal direction, a distal direction, or both a proximal direction and a distal direction.

2. The device according to claim 1, wherein each of the first plane and the second plane is perpendicular to a longitudinal axis of the shaft.

3. The device according to claim 1, wherein the second portion includes a port configured to apply suction for grasping a material.

4. The device according to claim 1, further comprising a locking mechanism corresponding to one or more of the first actuator, the second actuator, the third actuator, or the fourth actuator and configured to prevent rotational movement of the corresponding actuator.

5. The device according to claim 1, wherein the second actuator is distal to the first actuator.

6. The device according to claim 1, wherein the handle includes a port in communication with a lumen extending through the shaft and the articulation member, the lumen terminating at a distal opening in the first portion of the articulation member.

7. The device according to claim 6, wherein the port is proximal of the second actuator.

8. The device according to claim 6, wherein the lumen is configured to receive a tool.

9. The device according to claim 1, wherein a distal end of the second portion includes one of a port or a hook configured to grasp a tissue.

10. The device according to claim 1, wherein a distal end of the first portion includes an imager and an illumination device.

11. A medical device comprising:
- a handle, having:
  - a first actuator and a second actuator, each rotatable about a first axis of rotation;
  - a third actuator rotatable about a second axis of rotation different from the first axis of rotation; and
  - a fourth actuator rotatable about the first axis of rotation;
- a shaft coupled to the handle; and
- an articulation member integral with or coupled to a distal end of the shaft, the articulation member forming a distalmost end of the medical device and having a first portion coupled to a second portion,
- wherein the first portion is configured to articulate in a first plane and articulate in a second plane independently of the first plane wherein the first actuator and the second actuator are configured to control articulation of the first portion,
- wherein the second portion is configured to articulate in the first plane, independent of movement of the first portion in the first plane and or the second plane, wherein the third actuator is configured to control articulation of the second portion, and
- wherein the fourth actuator is configured to control proximal and distal movement of the second portion relative to the first portion.

12. The device according to claim 11, wherein the handle includes a port in communication with a lumen extending through the shaft and the articulation member, the lumen terminating at a distal opening in the first portion of the articulation member.

13. The device according to claim 12, wherein the lumen is configured to receive a tool.

14. The device according to claim 11, wherein a distal end of the second portion includes a hook configured to grasp a tissue.

15. The device according to claim 11, wherein a distal end of the first portion includes an imager and an illumination device.

16. The device according to claim 11, wherein the first actuator, the second actuator, and the fourth actuator are proximal of the third actuator.

* * * * *